United States Patent
Sauerland

[19]

[11] Patent Number: 5,942,100
[45] Date of Patent: Aug. 24, 1999

[54] CRYSTAL ETCH MONITOR

[75] Inventor: Franz L. Sauerland, Chagrin Falls, Ohio

[73] Assignee: Transat Corporation, Solon, Ohio

[21] Appl. No.: 08/918,300

[22] Filed: Aug. 25, 1997

[51] Int. Cl.$^6$ .................................. C25F 3/02; C25F 7/00
[52] U.S. Cl. ...................... 205/641; 205/645; 204/224 M
[58] Field of Search ...................... 205/645, 641; 204/224 M

[56] References Cited

U.S. PATENT DOCUMENTS 2,411,298  11/1946  Shore ........................................ 171/327

OTHER PUBLICATIONS

Sauerland, F. "Automatic Frequency Control in Chemical Etching of Quartz Crystal Blanks", publ. in the Proceedings of the 44th Annual Symposium on Frequency Control, 1990 (No Month).

*Primary Examiner*—Donald R. Valentine

[57] ABSTRACT

The present application describes apparatus and method for monitoring and controlling the etching of quartz crystals to a desired target frequency by means of monitoring the frequency of a monitor blank that is immersed in the etchant simultaneously with the etch load. Since during etching the thickness removal is the same for monitor and etch load, one can predetermine a monitor target frequency in terms of the load target frequency. The process is terminated upon reaching the monitor target.

6 Claims, 2 Drawing Sheets

CRYSTAL ETCH MONITOR

BACKGROUND OF THE INVENTION

The present invention relates to method and apparatus for automatic monitoring and control of the chemical etching of quartz blanks. In this process, the resonance frequency of the blanks is adjusted by immersing them in an etching solution. As the etchant thins the blanks, their resonance frequency increases.

The etch process includes two different stages:

A) an initial "nonlinear" stage, during which the blank frequency increases at a fast, nonlinear rate versus time. In this stage, the blank surface is cleaned of loose particles left from the preceding process step of lapping. The rate of frequency change is proportional to the initial roughness of the blank surface.

B) a subsequent "linear" stage, during which the blank frequency increases at a slower, linear rate versus time. In this stage, the blank thickness is reduced at a constant rate, provided the etchant's etch rate is constant.

In present practice, the etchant's etch rate cannot be held exactly constant because it is sensitive to variables such as temperature and concentration of the etchant. Therefore, present etching is a trial-and-error process: Typically, the blanks are exposed to the etchant for a predetermined time, after which they are cleaned, measured in air and, if they don't meet the target frequency, re-etched. This process is labor intensive and not amenable to precise frequency adjustment.

SUMMARY OF THE INVENTION

The present application describes apparatus and method for monitoring and controlling the etching of quartz crystals to a desired target frequency by means of monitoring the frequency of a monitor blank that is immersed in the etchant simultaneously with the etch load. Since during etching the thickness removal is the same for monitor and etch load, one can predetermine a monitor target frequency in terms of the load target frequency. The process is terminated upon reaching the monitor target.

The monitor blank can be made to suit different applications, including:

1) monitoring the etch rate of an etchant. In this application, the monitor blank frequency is monitored continuously in order to determine the etchant's etch rate. From this and the etch load targets specifications for the etch load one can determine the time required for controlling the etching of etch loads in the "linear" etch stage. The monitor blank is typically designed for long etch exposure, so that it can be used over multiple etch runs.

2) monitoring the etching of an etch load. In this application, the monitor blank frequency is monitored in order to determine its change during an etch run.

Since both monitor blank and etch load incur the same thickness removal during the run, the etch load's frequency change is directly related to the monitor's frequency change and can be adjusted by controlling the latter.

Monitor blank and etch load blanks need not be of the same type, but if they both have the same surface finish, the process can be controlled over both the nonlinear and linear etch stages. The monitor blank is typically discarded after the etch run.

BRIEF DESCRIPTION OF THE DRAWINGS

The invention may take form in various components and arrangements of components, and in various steps and arrangements of steps. The drawings are only for the purpose of illustrating preferred embodiments and are not to be construed to be limiting the invention.

DETAILED DESCRIPTION OF THE PREFERRED EMBODIMENTS

Figure 1:
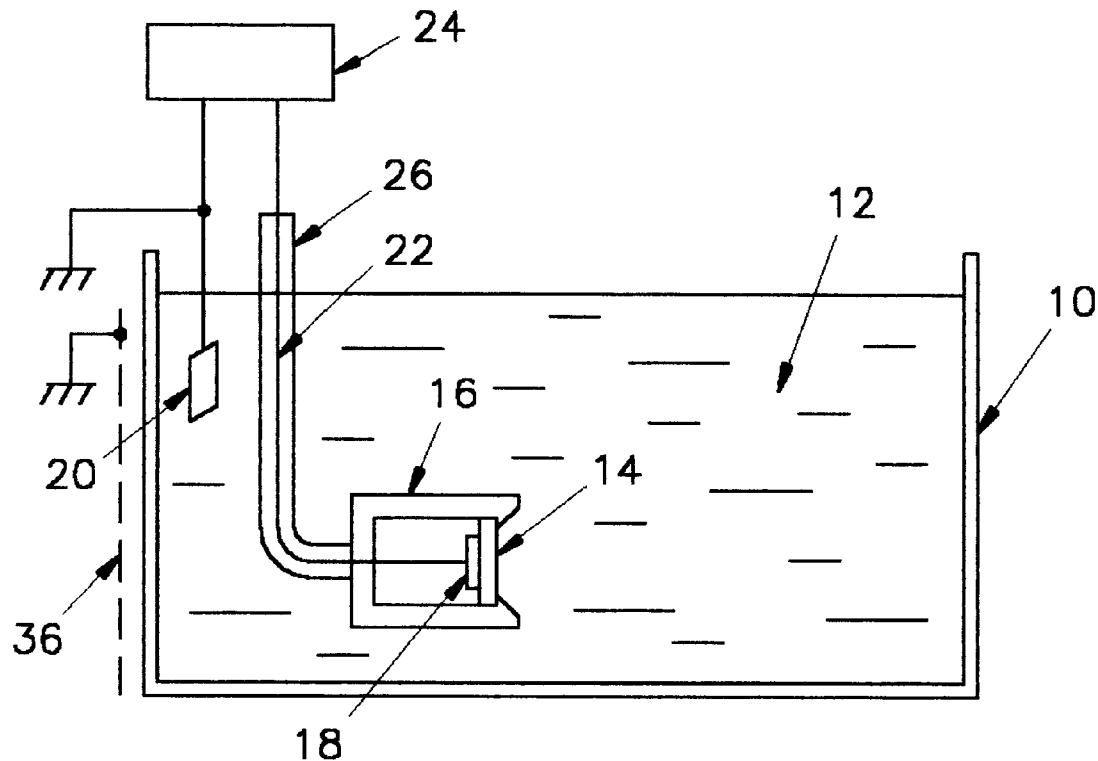
FIG. 1 illustrates a system according to the present invention.

With reference to FIG. 1, a tank 10 is filled with a liquid etching solution 12. A quartz monitor blank 14 is mounted in a sealed housing 16. A central area of a front face of the resonator blank is exposed to the etchant, and an electrode 18 is mounted to a center area of the rear face of the resonator blank and capacitively coupled to the blank. The electrode is connected via insulated wire 22 which is enclosed in a tube 26 that serves to isolate the wire and reduce the capacitance between the wire and the etchant. It also serves to equalize the internal pressure of housing 16 to the external pressure. This prevents a buildup of internal pressure when the probe is inserted into a hot etchant.

Wire 22 is connected to an instrument 24 for monitoring the resonance frequency of the blank. A return electrode 20 is immersed in the etchant and connected with measuring instrument 24 and ground.

Since electrode 20 is exposed to the etchant, it is subject to erosion. This can be prevented by insulating the electrode from the etchant while maintaining capacitive coupling to the etchant. One such embodiment would be to teflon-coat electrode 20. Another embodiment is to eliminate electrode 20 in favor of an external metal electrode 36 that is capacitively coupled to the etchant 12. In a third embodiment, tank 10 is surrounded by a water jacket contained in a grounded container. Since water has a high dielectric constant, it provides an effective capacitive coupling to ground.

Not shown in the Figure is an etch load of blanks, which is typically included in the etch tank. These blanks can be adjusted to a desired target frequency that can be mathematically related to and adjusted via the monitor target frequency. When the monitor target is reached, the etch run is terminated by extracting the etch load from the etchant. This can be done either by hand or by an automatic lift mechanism.

Figure 2:
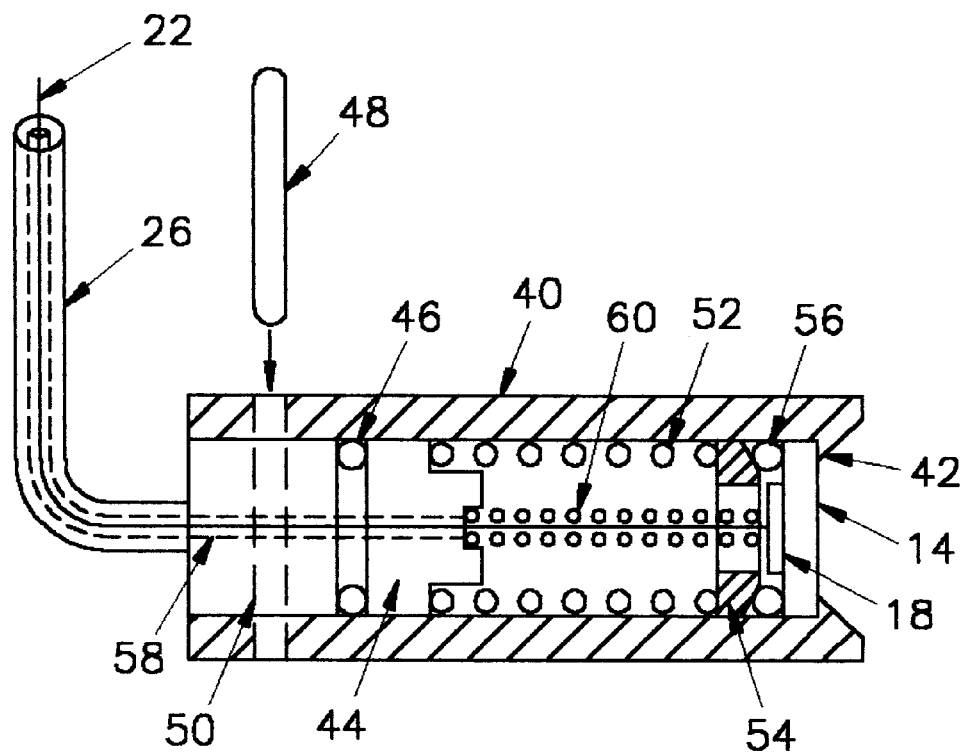
FIG. 2 shows a detailed example of one approach to mounting and housing the monitor blank.

FIG. 2 shows an example of a monitor probe designed for monitoring the etch rate of an etchant. It includes a monitor blank suitable for multiple etch runs. The probe 16 includes an outer housing 40 constructed of a material which is resistant to the etchant. The housing has an open front face with a ledge 42 that engages a front face of blank 14 at its periphery. A plunger 44 and an o-ring 46 seal a rear entrance of the housing 40 to the etchant. The plunger and seal assembly is held in place by a locking pin 48 inserted in a hole 50 drilled through the housing and plunger.

A first spring 52 extends from the plunger to bias a washer 54 against the rear surface of the blank, urging the blank against the ledge 42. The washer 50 has a 45 degree angle cut on its forward face which causes a resilient seal 56 to be pressed both against the housing surface and the periphery of the blank surface. This provides a hermetic seal which prevents etchant from flowing behind the blank. It also provides a resilient peripheral mounting for the blank, thereby minimizing the damping of the blank's resonance vibrations.

The wire 22 extends through a tube 26, through a bore 58 in the plunger, through an interior of the housing, and connects to a rear electrode 18. A second spring 60 biases the rear electrode 18 against the rear face of blank 14.

Figure 3:
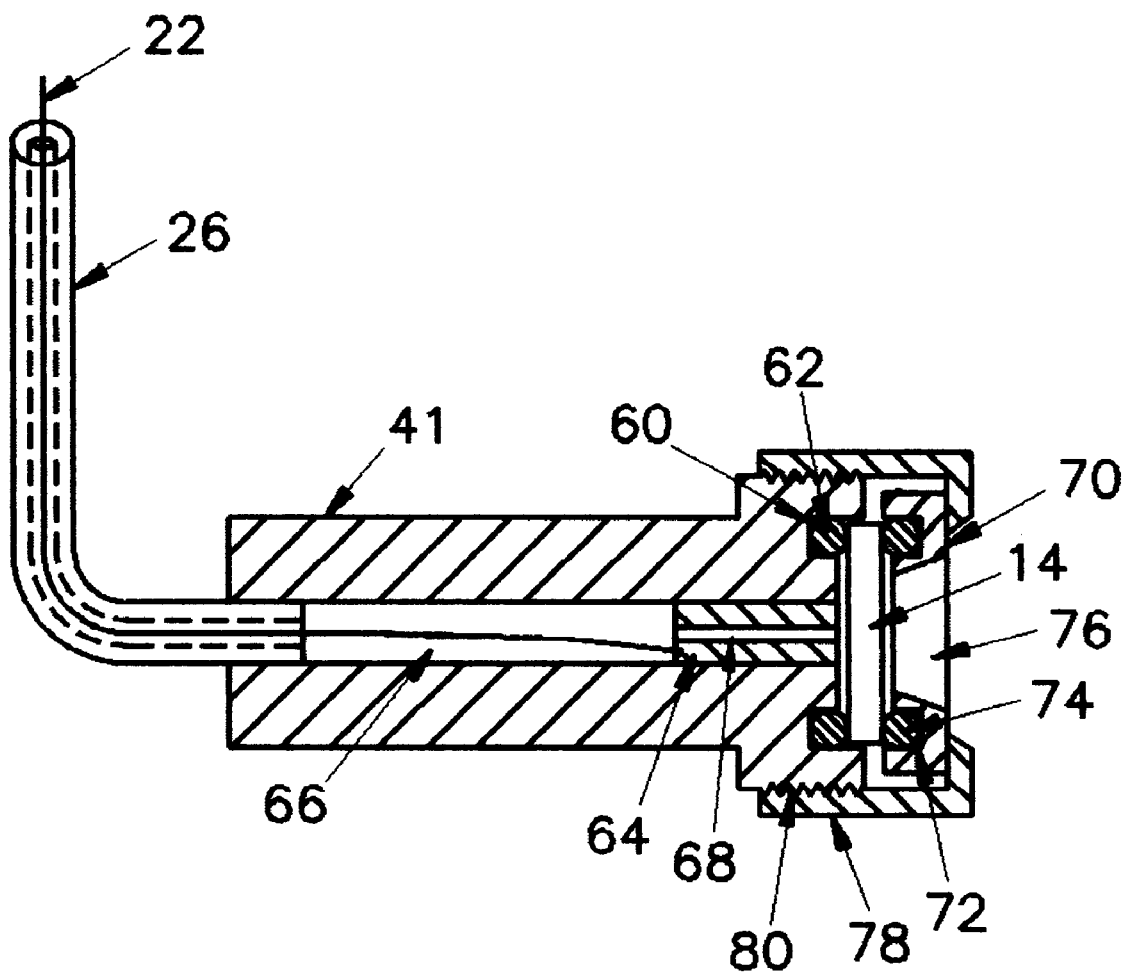
FIG. 3 shows a detailed example of another approach to mounting and housing the monitor blank.

FIG. 3 shows an example of a monitor probe designed for monitoring the etching of an etch load. It includes a monitor blank that is easily discarded and replaced after each etch run.

The probe 16 includes an outer housing 41 constructed of a material which is resistant to the etchant The housing includes an o-ring groove 60 and o-ring 62, and an electrode 64. The electrode is mounted inside a center bore 66 of the housing and includes a vent hole 68. The electrode is capacitively coupled to the blank via a small air gap between the adjacent surfaces of electrode and blank.

A tube 26, leads from the center bore 66 to the outside of the etchant. Inside tube 26 is a wire 22 that is connected to electrode 64.

A monitor blank 14 is seated between the o-ring 62 at its rear face and an o-ring 74 at its front face. O-ring 74 is contained in o-ring groove 72 of a pressure plate 70, which includes a center hole 76 for open access of the etchant to the front face of monitor blank 14.

Housing 41 is threaded by thread 80. A sleeve 78 is screwed onto thread 80, which allows the application of coaxial pressure to pressure plate 70 for clamping blank 14 at its periphery between o-rings 62 and 74 and thereby providing a hermetic seal and a low-damping mounting of blank 14.

Having thus explained main embodiments, the invention is now claimed to be:

1. A system for monitoring and controlling the etching of quartz crystals to a target frequency, the system comprising:
   a tank adapted to contain an etchant;
   a first electrode connected with a ground for galvanic connection with the etchant;
   a probe adapted for immersion in the etchant, the probe including:
      a sealed housing adapted to hold and enclose a quartz monitor blank and having an opening that exposes a central area of a front face of the blank to the etchant;
      elastic compression seals mountable to a periphery of front and rear faces of the blank to provide a hermetic seal between the housing and the mounted blank; and,
      a second electrode adapted to be capacitively coupled to the rear face of the blank; and,
   an instrument connected to the first and second electrodes for monitoring the frequency of the blank.

2. The system according to claim 1, further comprising means for terminating etching when the monitor frequency reaches a predetermined target value.

3. A system for monitoring and controlling the etching of quartz crystals to a target frequency, the system comprising:
   a tank adapted to contain an etchant;
   a first electrode mountable with the tank for electrical connection with etchant contained therein and connected with a ground;
   a probe adapted for immersion in the etchant, the probe including:
      a sealed housing having an interior cavity configured to hold and enclose a quartz monitor blank and having an opening that exposes a central area of a front face of the blank to etchant in the tank;
      a second electrode mounted in the housing cavity to couple capacitively to a rear face of the blank held in the housing cavity;
   an instrument connected to the first and second electrodes for monitoring the frequency of the blank; and,
   an air passage connected between the interior cavity of the probe and an exterior pressure for the purpose of equalizing an interior cavity pressure and the exterior pressure.

4. A method for controlling the etching of a load of quartz crystal blanks by monitoring the resonance frequency of a quartz crystal monitor blank submerged in an etchant, including the steps of:
   effectively connecting a first electrode with the etchant and ground;
   enclosing the monitor blank in a sealed housing that exposes a front face of the blank to the etchant;
   holding the monitor blank between two elastic compression seals peripherally around front and rear faces of the blank;
   capacitively coupling a second electrode to the rear face of the blank;
   connecting the first and second electrodes with a frequency measuring instrument outside the etchant; and,
   measuring the resonance frequency between the two electrodes.

5. Method according to claim 4, further including the steps of:
   determining a monitor target frequency in terms of the etch load specifications and the monitor start frequency;
   terminating the etch process when the monitor frequency reaches a predetermined target value.

6. A method for controlling the etching of a load of quartz crystal blanks by means of monitoring the resonance frequency of a monitor blank submerged in an etchant, including the steps of:
   connecting a first electrode with the etchant and ground;
   sealing the monitor blank in an interior of a housing so that a front face of the blank is exposed to the etchant;
   capacitively coupling a second electrode to a rear face of the blank;
   equalizing a pressure between the interior of the housing and an exterior pressure;
   connecting the first and second electrodes with a frequency measuring instrument outside the etchant; and,
   measuring the resonance frequency between the two electrodes.

* * * * *